United States Patent [19]

Turner

[11] Patent Number: 4,669,475
[45] Date of Patent: Jun. 2, 1987

[54] APPARATUS AND METHOD FOR HYPERTHERMIA TREATMENT

[75] Inventor: Paul F. Turner, North Salt Lake, Utah

[73] Assignee: BSD Medical Corporation, Salt Lake City, Utah

[21] Appl. No.: 750,408

[22] Filed: Jun. 28, 1985

[51] Int. Cl.$^4$ .............................................. A61N 5/02
[52] U.S. Cl. ................................... 128/399; 128/422; 128/736
[58] Field of Search ................ 128/804, 399, 422, 736

[56] References Cited

U.S. PATENT DOCUMENTS

| | | | |
|---|---|---|---|
| 4,190,053 | 2/1980 | Sterzer | 128/399 |
| 4,204,549 | 5/1980 | Paglione | 374/122 |
| 4,311,154 | 1/1982 | Sterzer et al. | 128/736 |
| 4,322,594 | 3/1982 | Brisson | 128/736 |
| 4,397,313 | 8/1983 | Vaguine | 128/399 |
| 4,397,314 | 8/1983 | Vaguine | 128/399 |
| 4,411,266 | 10/1983 | Cosman | 128/736 |
| 4,446,874 | 5/1984 | Vaguine | 128/804 |
| 4,448,198 | 5/1984 | Turner | 128/422 |

Primary Examiner—Edward M. Coven
Attorney, Agent, or Firm—Hubbard, Thurman, Turner & Tucker

[57] ABSTRACT

An applicator for radiating electromagnetic energy to local regions of body tissue where the applicator includes a radiation apparatus that emits electromagnetic radiation into the body tissue and further includes a temperature sensing apparatus that provides an indication of the adjacent body tissue temperature. In an embodiment, the applicator includes a thermistor connected between the center conductor and an outer conductor of a coaxial cable where the center conductor extends beyond the extension of the outer conductor for radiating electromagnetic energy. In another embodiment, a method is provided for operating the radiation applicator including the temperature sensor whereby direct current is provided across the applicator and the resulting direct current voltage is measured. The applicator is then supplied intermittently with high frequency electromagnetic energy. The voltage during the application of energy provides the power output of the applicator and the voltage during the absence of the energy provides a temperature indication of the surrounding body tissue. Still further, an electromagnetic hyperthermia system is provided that includes an electromagnetic radiation source connected to a plurality of radiation applicators that each include the temperature sensors. A control device is interconnected between the radiation source and the applicator that controls the radiation output from the applicators in accordance with the temperatures sensed and with a desired heating pattern.

12 Claims, 16 Drawing Figures

APPARATUS AND METHOD FOR HYPERTHERMIA TREATMENT

BACKGROUND OF THE INVENTION

1. Field of the Invention

The present invention relates generally to heating human or animal tissue (hyperthermia) and more particularly to electromagnetic radiation (EMR) apparatus for heating local areas within such living body tissue.

2. Background Information

As is generally known, death, or necrosis, of living tissue cells occurs at temperatures elevated above a normal cell temperature. Further, the death rate of such heated tissue is a function of both the temperature to which it is heated and the duration for which the tissue is held at such temperatures.

It is also well known that the elevation of temperature of living tissue can be produced with electromagnetic energy at frequencies greater than about 10 KHz.

It has been reported that some types of malignant cells may be necrotized by heating them to a temperature which is slightly below the temperature injurious to most normal cells. In addition, some types of malignant cells may be selectively heated and necrosed by hyperthermia techniques because masses of these malignant cells typically have considerably poorer blood flow and thus poorer heat dissipation properties than does the surrounding normal tissue. As a result, when normal tissue containing such malignant masses is heated by EMR (electromagnetic radiation), the resultant temperature of the malignant mass may be substantially above that of surrounding healthy cells.

Although some disagreement exists regarding exact temperatures, most malignant cells have a relatively limited temperature range in which hyperthermia is effective in causing necrosis. Below a threshold temperature of about 41.5° C. (106.7° F.) insubstantial thermal damage occurs even in those types of malignancies which have a greater sensitivity to temperature than do normal cells. In fact, at temperatures just below this threshold, growth of some types of malignancies may be stimulated. At temperatures within or above 43° to 45° C. (109.4° to 113° F.) thermal damage to most normal cells occur. A discussion of hyperthermia in the treatment of cancer is contained in "Physical Hyperthermia and Cancer Therapy" by J. Gordon Short and Paul F. Turner in the *Proceedings of the IEEE*, Vol. 68, No. 1, January, 1980 herein incorporated by reference.

Typically, EMR heating of body tissue is accomplished by holding an EMR radiator, or applicator, adjacent to, or against, exterior portions of a body, the EMR then penetrating and heating subsurface portions of tissue. However, significant amounts of energy are absorbed by surface or epidermis layers which may have to be cooled in order to prevent damage thereto by overheating.

The amount of penetration, or the depth of which EMR causes effective heating, is dependent upon the frequency of radiation.

For example, in accordance with an article by A. W. Guy, et al, published in proceedings of the IEEE, volume 63, No. 1, January, 1974 entitled "Therapeutic Application of Electromagnetic Power", the depth of penetration in the human muscle and fat at 100 MHz is 6.66 cm (2.62 inches) and 60.4 cm (23.8 inches), respectively, while at 915 MHz the depth of penetration is only 3.04 cm (1.2 inches) and 17.7 cm (6.97 inches), respectively.

In general, the lower the EMR frequency, the larger the applicator must be in order to effectively radiate electromagnetic energy into the tissue and, as a result, applicators for radiating electromagnetic energy below one gigahertz tend to be large in size and cumbersome to handle. Additionally, such applicators are not configured to selectively heat tumors of various sizes and shapes located well beneath the surface layers of the body being irradiated. Further, tumors, or other selected areas, shielded by a layer of boney tissue such as a skull, are different to effectively heat with externally applied EMR.

Invasive EMR applicators, that is, radiators which can be inserted into body tissue to levels adjacent malignant tumors, or other localized growths, for selective heating thereof, may cause nonuniform heating, or "hot spotting" at or near the surface of such applicators because of nonuniform field distributions. Such unwanted "hot spotting" is more likely to cause serious overheating when such invasive applications are operated at higher power levels in order to heat large localized growths using a single applicator. Such growths may be many times the size of the radiating area of an invasive type applicator.

An example of invasive EMR applicators are disclosed in U.S. Pat. No. 4,448,198 entitled "Invasive Hyperthermia Apparatus and Method" which discloses the application of several invasive type applicators and a method of using the apparatus to effectively heat relatively large localized areas within living body tissue, without significant hot spotting at or about the applicators.

The localized areas included those located well beneath surface layers of the body tissue. According to the disclosed method, the heating of these local regions within living body tissue were accomplished with a radiation source providing electromagnetic radiation to several applicators. Each of the applicators were adapted for insertion into the body tissue and for radiation electromagnetic energy therein.

In addition to the applicators, several invasive temperature probes were disclosed for monitoring temperatures within a target growth and also the normal tissue just outside the target growth.

It is the object of the present invention to provide an applicator for insertion into body tissue for radiation of electromagnetic radiation and for the detection of temperature therein.

It is a further object of the present invention to provide a system to provide radiation to the applicators in accordance with the sensed temperatures to control the heating of localized areas of body tissue.

It is still further an object of this invention to provide a system for controlling radiation provided to localized areas of body tissue by calibrating the applicator temperature sensor to determine the portion of measured temperature resulting from the heating of the applicator.

SUMMARY OF THE INVENTION

In accordance with the present invention an applicator is provided for radiating electromagnetic energy into local areas of body tissue. The applicator includes a radiation apparatus for emitting electromagnetic radiation into the body tissue that includes a temperature sensing apparatus for providing an indication of the adjacent body tissue temperature.

In one embodiment of the present invention, an applicator for radiating electromagnetic energy into the local regions of body tissues is provided that includes a coaxial cable having an outer conductor shorter in length than the center conductor whereby the temperature sensing apparatus is connected between the outer and inner conductors. In this embodiment, the temperature sensing apparatus includes thermistors each having an impedance at least 100 times greater than the impedance of the applicator at the electromagnetic operating frequency and distributed along the applicator to detect temperatures in different regions. Also in this embodiment, a metal cap is provided as a termination for this center conductor to increase the capacitance coupling of electromagnetic energy to the surrounding tissue.

In another embodiment of the invention, the center conductor termination cap includes a multidiameter metal tip. In this embodiment, the thermistor may be attached to the center conductor by being placed adjacent to the inner portion of the metallic tip and having another side of the thermistor connected to a high impedance lead which is then connected to the outer conductor.

In a further embodiment, a method for operating the hperthermia electromagnetic radiation applicator is disclosed that includes providing radiation energy to the application while simultaneously providing a direct current to the applicator for determining the surrounding tissue temperature.

Still further, a method for operating the hyperthermia electromagnetic radiation applicator that includes a temperature sensing device for indicating temperature variations in the surrounding body tissue is provided that includes the steps of providing direct current energy while simultaneously and intermittantly providing high frequency electromagnetic energy to the applicator. The voltage drop across the applicator is then measured both during the time that the electromagnetic energy is being applied and the time that the electromagnetic energy is absent. Since, in this method, the temperature sensing device absorbs a portion of the electromagnetic energy, the resulting measurements taken during the time that electromagnetic energy is absent are used to determine the temperature of the surrounding tissue. The measured voltage taken during the time of apllication of electromagnetic energy is used to determine the high frequency power output of the applicator.

In a still further embodiment of the present invention, an electromagnetic hyperthermia apparatus is provided for heating local regions of body tissue and includes a source of electromagnetic energy which is connected to a plurality of electromagnetic energy radiating applicators that are inserted in the body tissue. The applicators include temperature sensing devices for providing an indication of the temperature of the surrounding body tissue. A control apparatus is interconnected between the radiation source and each applicator that controls the radiation from each applicator in accordance with the temperature indicated by the applicator and a desired heating pattern. In operation, this control device varies radiation output from the applicators in order to produce the desired heating pattern as indicated by the temperature sensing devices in the applicators.

In one embodiment, the electromagnetic radiation applicators are connected to an applicator multiplexer which includes an attenuator controlled by the control device. The multiplexer enables one of several groups of applicators to be powered whereby the groups include different numbers of applicators. In an embodiment, the multiplexer includes transmission lines that electrically appear as an integral number of $\frac{1}{2}$ wavelengths of the source operating frequency.

BRIEF DESCRIPTION OF THE DRAWINGS

The novel features believed characteristic of this invention are set forth in the appended claims; however, this invention can be best understood by referencing the Detailed Description of the Embodiment together with these drawings.

DESCRIPTION OF THE PREFERRED EMBODIMENT

This invention relates to a system for the treatment of cancer by hyperthermia. Specifically, the system includes several microwave applicators that are inserted into living tissue around a cancerous growth. Microwave radiation is then distributed to these applicators which together provide microwave radiation which is used to heat the cancerous growth to a temperature which destroys the cancerous growth but leaves the normal living tissue surrounding the cancerous growth unharmed. In this invention, the microwave applicators include a microwave radiation capability and a temperature measuring capability enabling the system to provide radiation and determine the resulting heating of tissue surrounding the applicators.

Figure 1:
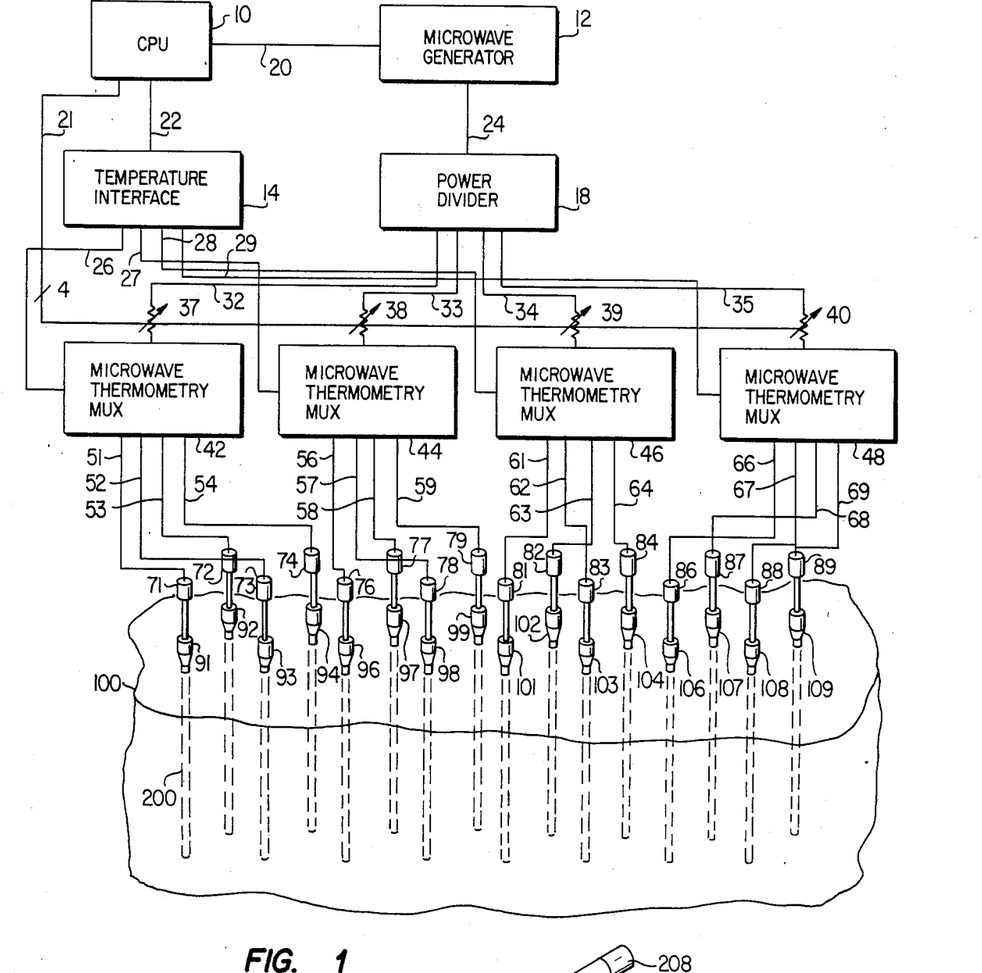
FIG. 1 is a block diagram of the electromagnetic hyperthermia apparatus.

FIG. 1 is a system block diagram of a typical system of the present invention. The system includes a microwave generator 12 that is connected by an RF power transmission line 24 to a power divider 18. The power divider 18 distributes RF power over lines 32, 33, 34, and 35 to four microwave thermometry multiplexers 42, 44, 46, and 48, where each thermometry multiplexer includes its respective attenuators 37, 38, 39, and 40. In the preferred embodiment, the microwave generator is a 915 megahertz generator (a model BSD 300). The microwave generator may also operate at 630 megahertz. In the preferred embodiment, a 50 megawatt 10 DB attenuator is used. Each multiplexer 42, 44, 46, and 48 is connected to four probes via RF transmission lines. For instance, the microwave thermometry multiplexer 42 is connected to four RF transmission lines 51-54 that are respectively connected to four applicators 71-74. The applicators are inserted inside four catheters 91 to 94 which have been placed in the human tissue 100 around the area to be heated.

The amount of power provided to each applicator is controlled by its respective multiplexer's attenuator. The control of the attenuator may be manual or may be controlled by a central processing unit 10. In FIG. 1, the four attenuators 37-40 are each connected to one of the four lines represented by a single line 21 which is, in turn, connected to the central processing unit 10. In this manner, the central processing unit 10 controls the amount of RF power distributed to each of the multiplexers 42, 44, 46, and 48. It should be understood that the attenuators may also be replaced by any means for regulating power distribution to the multiplexer such as switches, amplifiers, mismatched tuning sections or the like.

The applicators 71-74, 76-79, 81-84, and 86-89 all include temperature sensors. The temperature sensors are also connected to the microwave thermometry multiplexers 42, 44, 46, and 48 through the respective lead lines as shown. The output of the temperature sensing devices then connected to the temperature interface circuitry 14 via lines 26, 27, 28, and 29 from the connected multiplexers as shown. The temperature sensor information is then provided to the central processing unit 10 via line 22. In practice, the output of the microwave thermometry multiplexer may be a single multiplexed line for all the sensors connected to the multiplexer or it may be individual discrete lines from each of the applicators to the temperature interface circuitry 14. The central processing unit 10 will be able to adjust the amount of radiated power to the applicators in accordance with the indicated temperature to treat the tissue area with a predetermined heating pattern. During treatment, the central processing unit 10 will monitor the indicated tissue temperature from the applicators and make whatever adjustments are necessary to the radiated power distributed to the applicators.

The implementation of the timing of the RF power and temperature monitoring is important to insure the accuracy of heating of the tissue.

In one implementation, power is applied to the individual applicators while temperature is measured. Power is then turned off to allow the temperature sensors to cool wherein again temperature is measured. Since the tissue requires more than two seconds to substantially cool, by turning the power off the temperature may be accurately measured since the temperature sensors will normally cool off much faster then the two seconds. By alternately switching RF power on and off from the microwave generator 12, the temperature sensors may be calibrated to determine what portion of the temperature increase during the power on is caused by the heating of the temperature sensors themselves. The central processing unit is then used to regulate the amount of power applied to each of the applicators to produce a specified heating pattern in the body tissue 100. If the temperature sensors do not heat up sufficiently to result in a discrepancy of reading during the application of RF power, the temperature measured during the application of RF power to the body tissue 100 will be used to control the resulting heating pattern.

A further system enhancement includes the independent control of amplitude and phase to control the heat pattern. This would improve the capability to provide the desired heat patterns.

MULTIPLEXER

Clinical use of this system of FIG. 1 will vary in the number of applicators actually required for use. Typically, between 1 and 16 applicators will be used. To improve clinical use and speed of the changing of the number of applicators, a novel multiplexer will be used. The probes will attach to a coax quick disconnect connectors to the multiplexers. Typically, 4 multiplexer modules will be used. Each multiplexer contains passive one-way, two-way, three-way, and four-way multiplexing circuits. If the operating frequency of the system (the operating frequency of the microwave generator 12) is fixed, each of the multiplexers may be fabricated such that each multiplexing circuit includes a transmission line length that is an integral number of half wavelengths of the operating frequency resulting in the nonconnected lines appearing as an open circuit to the RF transmission lines.

Figure 2A:
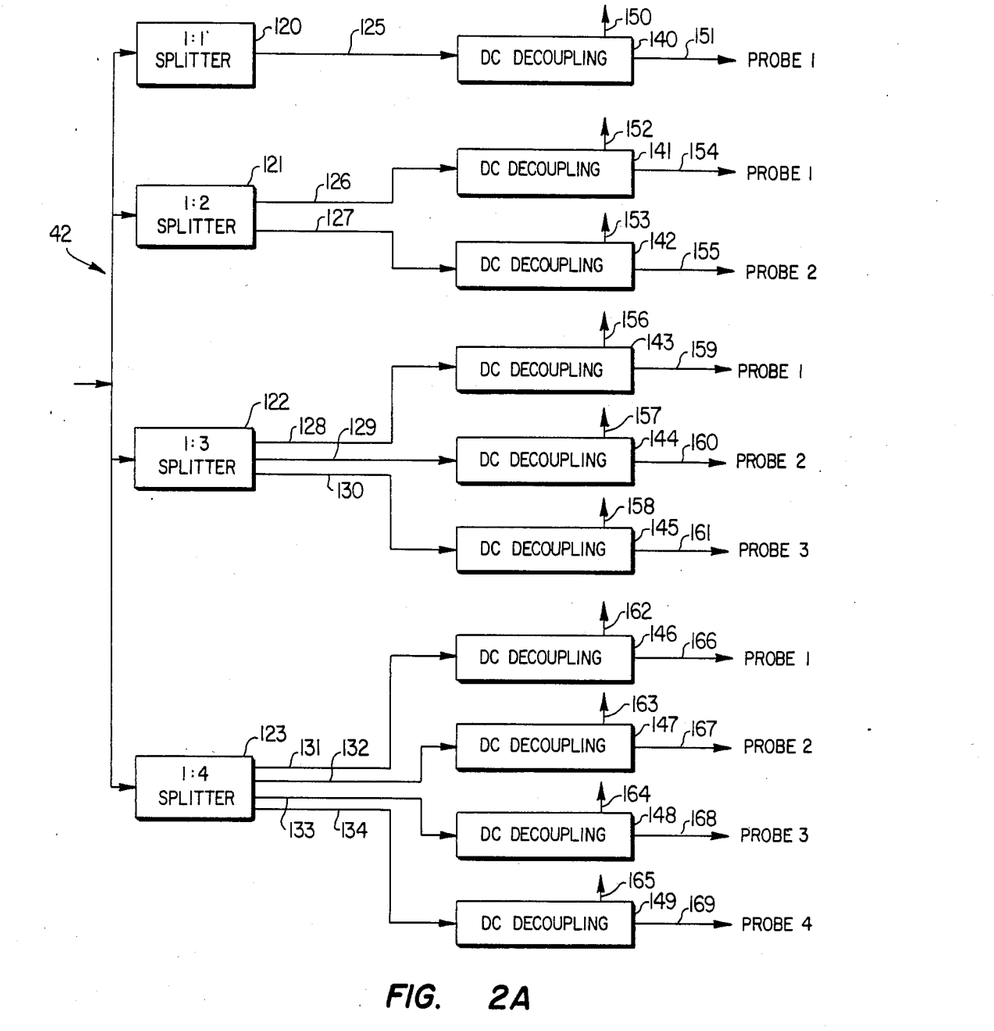
FIG. 2A is a block diagram of the applicator multiplexer.

FIG. 2A is a block diagram of multiplexer 42. In practice, multiplexer 42 is identical to multiplexers 44, 46, 48. Multiplexer 42 includes the just discussed 1:1 splitter 120, 1:2 splitter 121, the 1:3 splitter 122, and the 1:4 splitter 123. The different splitters 120 to 123 allow the use of a single probe per multiplexer up to four probes per multiplexer. Each probe is connected to an individual decoupling circuit such as 140 to 149 as shown. The DC decoupling circuits includes a simple capacitance and inductance to provide a DC direct current signal on the DC line such as 150 which may be multiplexed or discretely connected to the temperature interface circuitry previously discussed. The DC coupling circuitry 140 further provides the RF connection between the splitter 120 via lien 125 to the probe via line 151 as shown. In this manner the probe receives the RF power while providing a direct current temperature sensing indication signal.

Figure 2B:
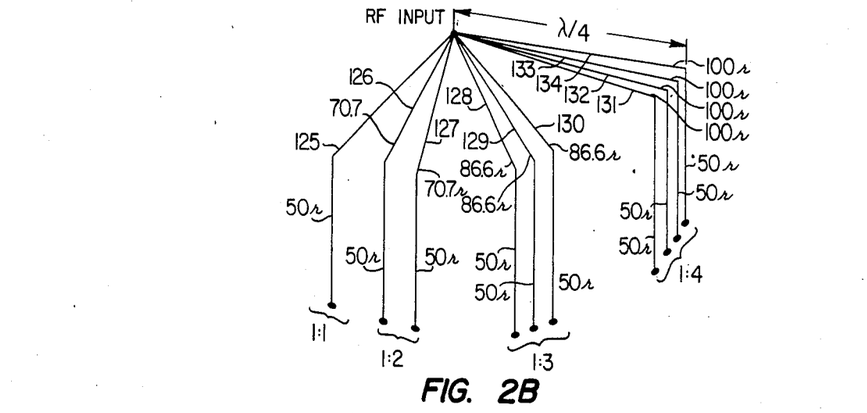
FIG. 2B is a diagram illustrating the internal resistances of one applicator multiplexer embodiment.

In the embodiment shown in FIG. 2A, each of the splitters 120-123 includes the connection to a unique group of connectors 1-4 as shown. One embodiment of the splitter arrangement 120-123 is illustrated in FIG. 2B. It is important to understand that the unused splitter sections must appear to the RF input as an open circuit. To accomplish this the transmission distance between the connector and the RF input is structured to be an integral number of one-half wavelengths of the operating frequency. In the diagram of FIG. 2B, the resistances for the different lines splitters of FIG. 2A are shown. For example, the 1:1 splitter includes a 50 ohm impedance from the RF input to the probe connection. The 1:2 splitter includes the two 50 ohm leads connected to two lines 126 and 127 each having an impedance of 70.7 ohms a piece. Likewise, the 1:3 connection includes three lines 128, 129, and 130 each having an 86.6 ohm impedance. The 1:4 connection includes four lines 131 to 134 each having a 100 ohm impedance. These matching sections 125–134 should each pesent a transmission length of ¼ wavelength of the operating frequency. The overall connection again is ½ wavelength or an even multiple of ½ wavelengths at the operating frequency from the RF input to the applicator connection when unconnected. When probes are connected, the resistances are not sufficiently different from the applicator impedance of 50 ohms to result in a impedance mismatch problem. The impedance of the matching sections of the multiplexer, in the preferred embodiment, is a function of the width of this lines strips and of the thickness of the dielectrics. By varying the conductor line width, various impedances may be fabricated on a single printed circuit board for the different groups of line splitters.

Figure 2C:
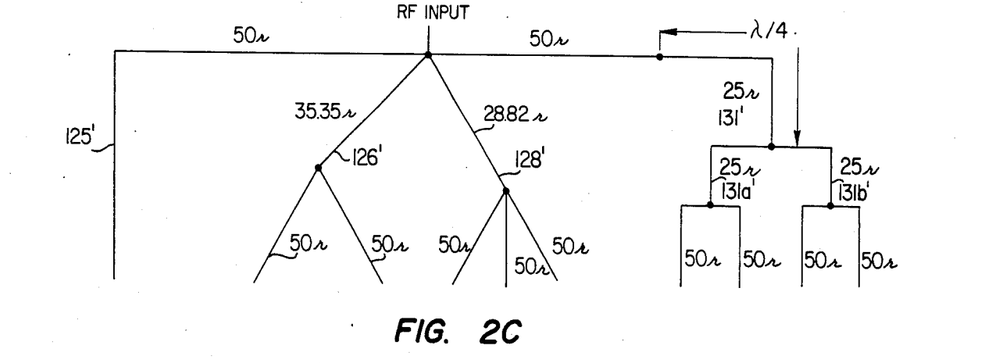
FIG. 2C is a resistance diagram of a second embodiment of the applicator multiplexer.

A second embodiment is illustrated in FIG. 2C where the matching sections such as 126' and 128' include single lines directly connected to the RF input for the groups of applicators.

Figure 2D:
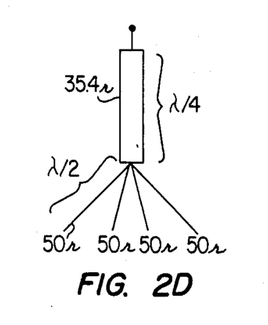
FIG. 2D is a resistance diagram of a third embodiment of the applicator multiplexer.

FIG. 2D illustrates a third embodiment including a single matching section of 35.4 ohms and appearing as a ¼ wavelength of the operating frequency between the RF input and ½ wavelength leads each having 50 ohms. The uniqueness of the FIG. 2D structure is that anywhere from 1 to 4 applicators, each applicator having a 50 ohm impedance, may be connected without an excessive impedance mismatch. In the preferred embodiment, the voltage standing wave ratio is preferred to be not gerater than 2:1. The embodiment of FIG. 2D will provide an impedance matching for up to four probes with a VSWR not greater than 2:1.

Figure 2E:
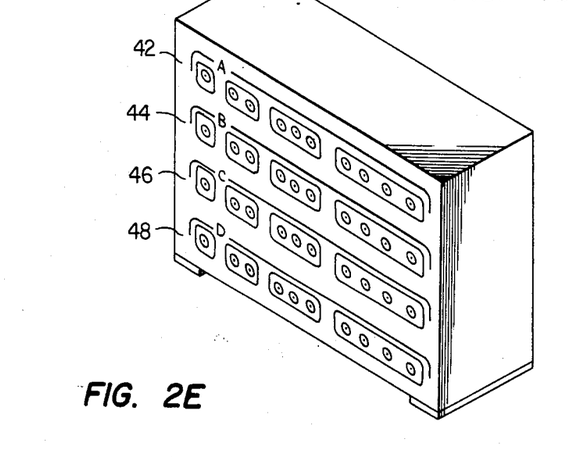
FIG. 2E is a plan view of a chassis containing four applicator multiplexers.

FIG. 2E is a planned view of the multiplexers 42, 44, 46, and 48 contained in a single cabinet. In this embodiment the multiplexer diagram of FIG. 2B has been implemented such that individual groups of applicators must be connected at the respective connection points.

APPLICATOR

Figure 3:
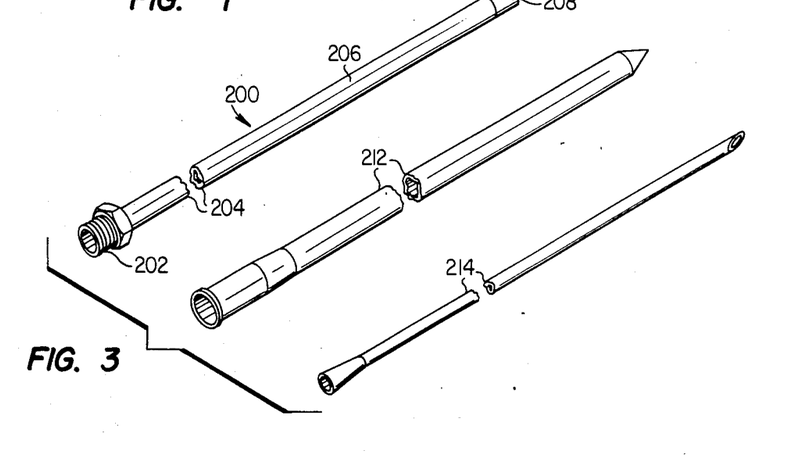
FIG. 3 is a plan view of a radiation applicator, a catheter and a hyperdermic needle.

FIG. 3 illustrates the applicator 200 together with a catheter 212 and a hyperdermic needle 214. In the preferred embodiment, the catheter 212 is dry catheter (i.e. closed tip) and will be inserted into the body tissue. In practice, the catheter is an 16 gauge catheter. The applicator 200 will then be inserted inside the catheter 212. The applicator 200 includes the connection 202 and a coaxial cable shown as 200 having an outside coating 206 and terminating with a tip 208. The hypodermic needle 214 is provided to indicate the relative size of the applicator and catheter. A blunt tip needle can be used inside the catheter to stiffen the catheter during insertion into the tissue and then removed.

Figures 4A, 4B:
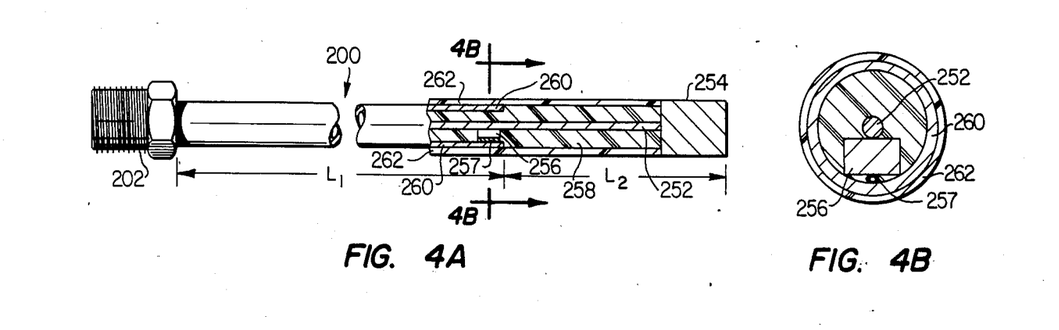
FIG. 4A is a partial sectional view of a radiation applicator.
FIG. 4B is a cross-sectional view of the radiation applicator of FIG. 4A.

The interior of the applicator is illustrated in FIG. 4A as a partial cross-sectional view. The connector 202 is connected to a lead line as shown in FIG. 1. FIG. 4A illustrates that the applicator consists of two lengths L1 and L2, where L1 is the length of the outside conductor shown as 260 and L2 is the length of the exposed center conductor 252 portion including the metallic tip 254 connected to the center conductor 252. The conductor 260 includes a coax outer dielectric sleeve 262 covering the coax outer conductor 260 and extending down to the metallic tip 254. Inside the outer conductor 260 is a dielectric material 258 and the center conductor 252.

Shown in this embodiment is a thermistor 256 that is connected to the center conductor 252 directly and connected to the outer conductor 260 by a resistor pad 257. The cross-section view of FIG. 4B illustrates this interconnection of the thermistor 256 in more detail. In practice, the applicator provides RF radiation through the center conductor 252, metal tip 254 and the outside conductor 260 while providing a temperature indication of the region from the resulting resistance of thermistor 256. Here the outer conductor 260 is cut back from the tip to expose the radiating center conductor 252 as shown. This applicator includes the addition of a five mega ohm thermistor 256 between the center conductor 252 and the outer conductor 260 to enable the measurement of temperature. In practice, the thermistor 256 is a microscopic chip that is inserted in place of the dielectric 258 connected to the center conductor 252 and the outer conductor 260 as shown. This process requires removal of a portion of the dielectric 258 insulator to expose the center conductor 252 to provide the connection. However, when assembled the thermistor 256 connection to the center conductor 252 does not result in an increase in the overall diameter of the probe as shown. Therefore, the probe may be still inserted into a catheter as before. The resistance of the thermistor 256 changes as temperature changes. Therefore, by placing a DC voltage across the outer conductor 260 and center conductor 252, the resulting measured resistance indicates the temperature of the region.

The location of the thermistor underneath the outer conductor and connected to the interconductor results in a higher thermistor artifact or heating of the thermistor because of the presence of the RF field. However, by determining the slopes of cooling, the heat resulting from the thermistor artifact may be distinguished from the temperature of body tissue.

In one embodiment where the thermistor is located at the end of the outer conductor, the actual tissue temperature would be measured when RF power is low or 0 to avoid additional temperature rise of the thermistor while the thermistor is exposed to the RF fields. Since the resistance is measured, the change in resistance resulting from an implied RF power field may be used to measure the power. The DC resistance is the same as the RF resistance for very small chip thermistors. It is important to use a high impedance thermistor to avoid excessive thermistor heating. By using a thermistor small enough to be substantially heated by typically applied RF power, the rapid heating response of the small thermistor to the RF power can be distinguished from the slower tissue temperature rise. Since the applicator is generally used inside a dielectric catheter, the thermal time constant of the sensor to the outer tissue heating is typically two seconds or more. The thermal response time of the thermistor to its own heating from RF energy is much faster however. The timing of a power input pulse with, before, during, and after readings can provide a measure of both the RF voltage at the probe radiating tip and the neighboring tissue temperature. The measured RF voltage field would provide a relative measure of the RF power radiated from each of the several applicators in array. Thus the radiating power balance could be obtained for several applicators as well as the tissue temperatures near each.

Figure 4C:
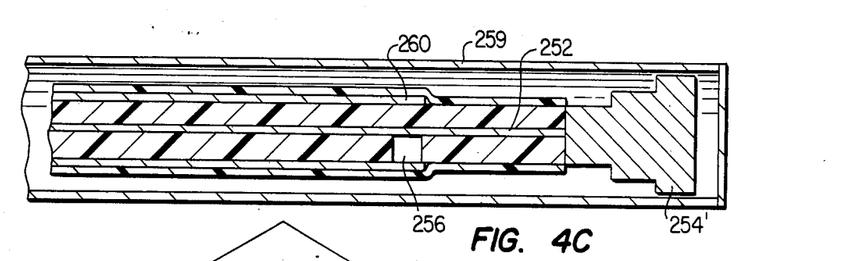
FIG. 4C is a partial cross-section view of a second embodiment of the radiation applicator.

FIG. 4C illustrates a second embodiment of the applicator whereby the tip 254' tip includes several diameters progressively stepped as shown. The use of the metal tip 254 and the metal tip 254' increases the capacitive coupling of the RF power towards the tip resulting in a more uniform and heat distribution to the body tissue towards the tip.

Figure 5:
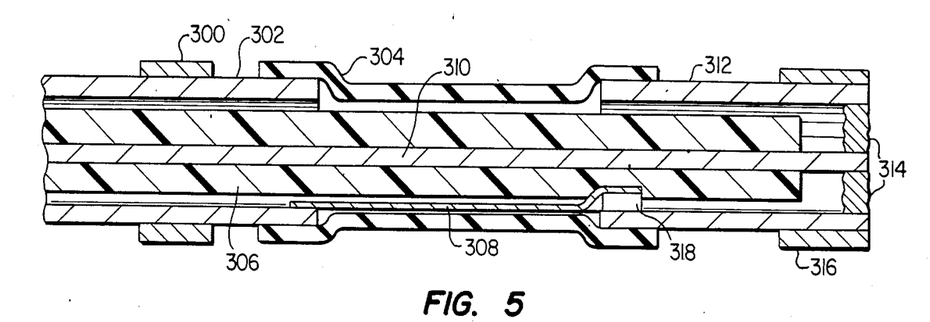
FIG. 5 in a cross-section view of a radiation applicator illustrating a different interconnection scheme of the temperature sensing thermistor.

A third embodiment of the tip structure is illustrated in FIG. 5. Here the outer conductor 302 extends as before and is surrounded by an enlarged diameter metal ring 300. The center conductor 310 extends to a meal tip which consists of a second enlarged metal ring 316 connected to the center conductor 310 by a solder connection 314. Underneath the second enlarged ring 316 is the metal tip 312 that extends back towards the outer conductor. The thermistor 318 is connected to the tip 312 to provide the connection to the center conductor 310. A high resistive carbon lead 308 connects the other side of thermistor 318 to the outer conductor 302 as shown. The portion of the applicator between the metal tip 312 and outside conductor 302 includes heat shrink insulator tubing 304. In this manner the thermistor is placed further down the adapter for the measurement of temperature and is not exposed to excessive RF heating as the embodiment of FIG. 4. In this preferred embodiment, the thermistor 318 is placed 1 centimeter towards the tip 312 from the break in the outer conductor 302 so as to be away from the intense microwave field inside the outer conductor 302. The tip 312 is 2.9 centimeters long so that the thermistor is still substantially within the applicator heating pattern being 1.9 centimeters from the applicator end. The thermistor is connected to the center conductor 310 via a metal tip sleeve 312 which is 1.9 centimeters long which is then soldered to the center conductor. The other side of the thermistor 318 is connected to the outer coax conductor 302 through a thin carbonized lead 308 having high resistance typically 200 to 1 megaohm. Since the RF radiation resistance is about 50 ohms, and the high resistive lead 308 is in parallel to the center conductor 310 (space within a thin dielectric), the shunt capacitance between the resistive lead 308 and the center conductor 310 provide a distributed resistance and capacitance network as shown in FIG. 6.

Figure 6:
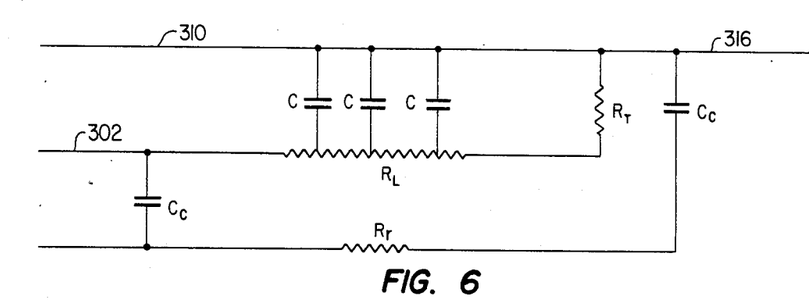
FIG. 6 is a schematic diagram of the radiation applicator.

In FIG. 6 $R_t$ is the thermistor resistance, $R_1$ is the resistive lead resistance, C is the distributed shunt capacitance, $R_r$ is the radiation resistance and $C_c$ is the catheter wall capacitance. This circuit of FIG. 6 shows that when $R_t$ and $R_1$ is high, at high frequencies the capacitive impedance between the inner conductor and the resistive lead will filter the amount of the RF current reaching $R_t$. Since the whole circuit is loaded with the radiation resistance $R_r$ through the catheter wall capacitance $C_c$, the only DC resistance measured is $R_t$ in series with $R_1$. So $R_1$ should be much less than $R_t$ so as not to substantially modify the temperature dependence of $R_t$. However, $R_1$ should be high enough to provide some RF current filtering to reduce thermistor heating. In the preferred embodiment, the 5 mega ohm thermistor (at 25°) has been tested and its value at 52° is 2 mega ohms.

The advantage of this structure is that the thermistor will measure the temperature of the surrounding area without regard to the RF power level. In other words, the thermistor RF heating is minimal. This means that the temperature sensors may be easily calibrated. Testing of the prototypes of this design resulted in the amount of local thermistor and applicator heating observed to be much less than 1° at typical clinical power levels at 5 watts. In comparison, the applicator of FIG. 4 with the installation of the miniature thermistor chip between the center and outer conductor results in a 9° selective temperature rise with 5 watts. In this embodiment (FIG. 8), the thermistor is placed nearest the hottest tissue heating point at the very end of the outer conductor. Here the electric field is very concentrated as well as the current flowing into the center conductor. The thermistor temperature is primarily a result of three parts: thermistor heating, coaxial center conductor heating, and surrounding tissue heating. The mass of the surrounding tissue is much larger than the mass of the thermistor, metal cover and outer conductor. When RF power is turned off, the thermistor and conductors will cool much faster than the tissue. The interconductor heating therefore is the highest. From testing it was determined that the outer conductor heating is 16% of the heating of the interconductor. The thermistor heating is only about 5% of the conductor heating. The measured response of cooling for the prototype applicators were observed to be typically below 250 milliseconds after the RF power had been turned off. The amount of temperature rise in these parts with 10 watts power input is typically 15° above the tissue temperature. This can be calculated by measuring the resistive change of the thermistor with a DC decoupling circuit remotely located on the RF power input circuit (the multiplexer as previously discussed). This temperature change may be used to measure the relative radiating power from each applicator. The resistive equation for the themistor is:

$$R = Ae^{(D/T)}/T^c$$

where R is the resistance, T is the temperature in Kelvin degrees, and A, D, and C ar constants found by a three temperature calibration technique. The general form of this equation can be approximated by:

$$AT^2 + TB + C = T^2 \ln(R)$$

When R is measured at three different temperatures, the constants of calibration may be found by solving the three equations simultaneously.

The change in temperature is directly proportional to the power input. So the power balance can be determined by comparing the relative temperature changes, observed as the RF power is turned off for about one second. In an array these temperature change measurements could guide an operator in monitoring adjustments of the power balance of several applicators. Having measured the various temperature changes of cool down after RF powers turned off, these values can be subtracted from the measured temperatures while the power is on. If the total input power is changed to all applicators, the resulting change in temperature expected on all the applicator temperature sensors could be estimated as being proportional to the power change until the next RF power off sequence (typically every 30 seconds).

Figure 7A:
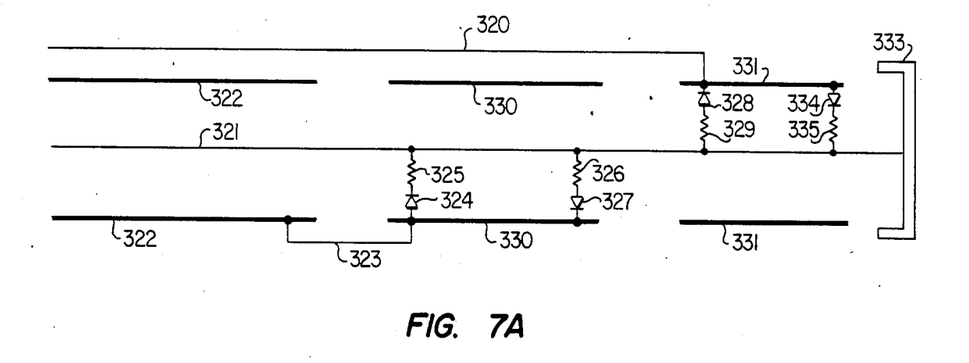
FIG. 7A is a diagram illustrating an applicator including several temperature sensors.

FIG. 7A illustrates a further embodiment of the present invention wherein several thermistors 325, 326, 329 and 335 are connected to a single applicator. In this embodiment, the outer conductor 320 extends down to a certain point where it breaks, a second section of outer conductor 330 is provided. In this embodiment, the first outer conductor 322 is connected to the second outer conductor 330 via a high resistive lead 323. In the second section 330 two thermistors 325 and 326 are located at either ends. In practice, a DC current is provided in one direction to the outside conductor 322 and the resulting DC voltage is measured between the outside conductor 322 and the center conductor 321. The current is provided in one direction for one thermistor and in the opposite direction for the second thermistor. For example, a current flow from the outer conductor 322 to the interconductor 321 would provide a current flow through diode 324 and thermistor 325. Therefore, the measured resistance of thermistor 325 would provide an indication of the temperature at that location. A current flow from the center conductor 321 to outer conductor 322 would provide a flow of current through diode 327 and thermistor 326 to provide an indication of the temperature at the location of thermistor 326. In other words, the diodes 324 and 327 together with the direction of current flow, provide a means to measure temperature indicated by the resistance of two separate thermistors. Also, illustrated in FIG. 7A is a further embodiment that includes a high resistive lead 320 that is not connected to the outer conductors 322 and 330 but connected to a third outer conductor section 331. This outer conductor section again includes a thermistor 329 and a diode 328. However, in this embodiment another thermistor 335 is located in the area of the center conductor connected metal tip 333. As before, the thermistor 335 includes a diode 334 and is connected by a high resistive lead 332 to the outer conductor section 331. As previously described a DC current provided on lead 320 may be used with the center conductor 321 to measure the temperatures of the regions of the two thermistors 329 and 335.

Figure 7B:
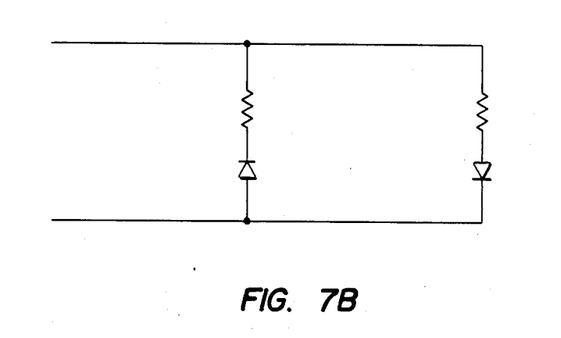
FIG. 7B is a schematic diagram of the temperature sensor arrangement of FIG. 7A.
Figure 7C:
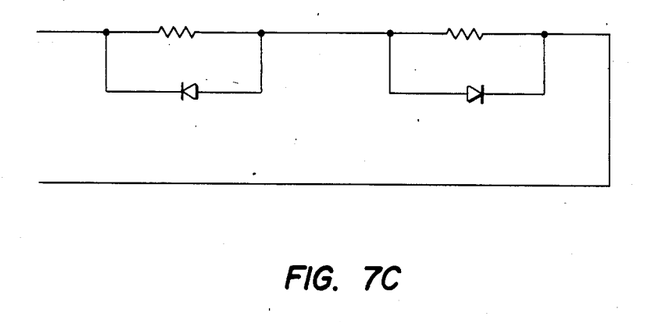
FIG. 7C is a schematic diagram of a second embodiment of the multiple temperature sensor structure.

The diodes and thermistors may be provided in either a parallel configuration as illustrated in the schematic of FIG. 7B. The parallel configuration is also that of FIG. 7A. FIG. 7C illustrates a further embodiment where the thermistors are in series but include diodes that act as current bypass devices for the different current directions.

A further embodiment of this invention includes an applicator having a fiberoptics temperature sensor contained in the dielectric. The temperature sensor would be connected to the multiplexer by fiberoptic lines. A fiberoptic structure for measuring temperature is illustrated in U.S. Pat. No. 4,136,566 which is herein incorporated by reference. Other means of optically determining temperature are disclosed in the paper entitled "Thermometry Considerations in Localized Hyperthermia" by T. C. Cetas and W. G. Conner printed in Medical Physics, March/April, 1978. By placing a fiberoptics temperature sensor and fiberoptic connecting lines in the dielectric of the radiating applicator, the temperature along several different regions may be measured without providing any electrical disturbance to the radiating portion of the applicator.

Figure 8:
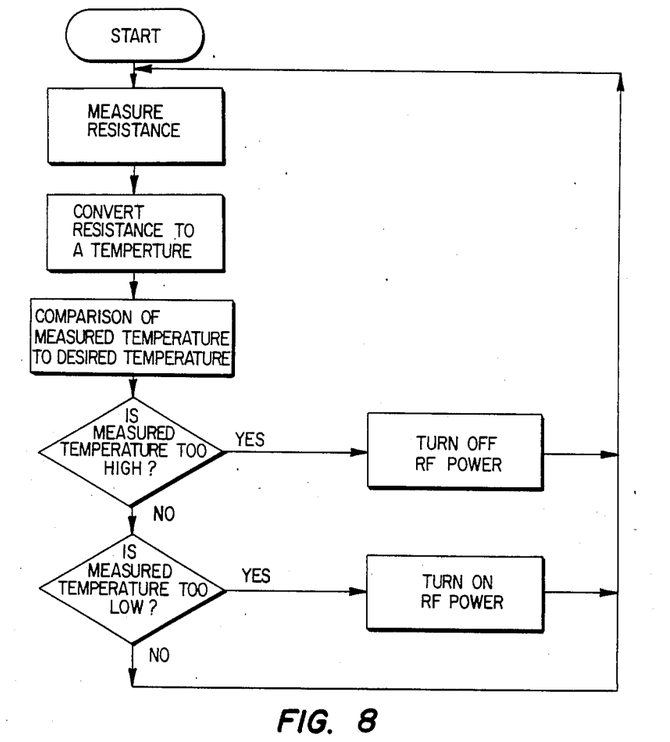
FIG. 8 is a software flowchart of the software used to calibrate the temperature sensing thermistor of the radiation applicators.

FIG. 8 illustrates a software flowchart of the software that would be normally executed by the central processor unit 10 of FIG. 1. The CPU uses the temperatures measured at the applicator locations to adjust power transmitted to conform to a preselected heating pattern. Using applicators with several temperature sensors, a three dimension heating pattern may be detected which, with attenuator and phase relationship adjustments, may be used to more exactly provide treatment.

Although preferred embodiments have been described in detail, it should be understood that various substitutions, alternations and changes may become apparent to those skilled in the art. These modifications may be made without departing from the scope and spirit of the invention as defined by the appended claims.

What is claimed is:

1. An electromagnetic hyperthermia system for heating local regions within living body tissue comprising:
   (a) a microwave generator for producing microwave energy at a preselected frequency;
   (b) a power dividing means operatively connected to the microwave generator for dividing the microwave energy selectively for distribution;
   (c) a multiplexing means including a plurality of multiplexers and a microwave energy control means operatively connected to the power dividing means for controlling the amount of microwave energy to be multiplexed by the plurality of multiplexers;
   (d) applicator means operatively connected to the multiplexing means for radiating the microwave energy into surrounding body tissue, the applicator means including a plurality of applicator groups operatively connected to the plurality of multiplexers, and a temperature sensor means operatively connected to the applicator means for producing signals indicative of the temperature of the body tissue during heating; and
   (e) a control means having a preselected temperature reference signal producing means operatively connected to the temperature sensor means and microwave energy control means of the multiplexing means, said control means responsive to the reference temperature signal and signals of the temperature sensor means for producing microwave energy control signals for adjusting the amount of radiated microwave energy multiplexed to each applicator of the plurality of applicator groups whereby the distributed microwave energy is radiated sufficiently to treat the tissue area with a predetermined heating pattern for destroying cancerous growth while leaving unharmed the normal living tissue surrounding the cancerous growth.

2. An electromagnetic hyperthermia system according to claim 1 wherein the microwave energy control means of the multiplexer means includes a plurality of microwave energy regulators taken from the group consisting of attenuators, switches, amplifiers, and mismatched tuning sections.

3. An electromagnetic hyperthermia system according to claim 1 wherein each multiplexer of the plurality of multiplexers includes a plurality of microwave energy splitters responsive to the incoming microwave energy for producing microwave energy for a preselected number of applicators operatively connected to the multiplexer.

4. An electromagnetic hyperthermia system according to claim 3 wherein the plurality of microwave energy splitters includes passive one-way, two-way, three-way and four-way microwave energy splitters having transmission lines of half wavelengths sufficient for impedance matching between the applicators of the group of applicators and the microwave energy splitters whereby the unused splitters appear as an open circuit to the microwave input.

5. An electromagnetic hyperthermia system according to claim 3 wherein each microwave energy splitter of the plurality of microwave energy splitters includes a single microwave energy quarter wavelength matching section between the microwave energy input connector and half wavelength leads and a preselected resistance whereby a preselected number of applicators may be connected to the half wavelength leads without impedance mismatch.

6. An electromagnetic hyperthermia system according to claim 1 wherein each multiplexer of the plurality of multiplexers includes a decoupling means for determining the direct current voltage drop across the applicator indicating the body tissue temperature, said decoupling means operatively connected to the control means.

7. An electromagnetic hyperthermia system according to claim 1 wherein each applicator of the plurality of applicator groups include an outer conductor and an inner conductor, the inner conductor having an end portion extending beyond an end of the outer conductor, a conductive tip connected to the end of the inner conductor, a temperature sensor means interconnecting the outer and inner conductors, and means for connecting a dc voltage across the outer and inner conductors whereby a measure of the resistance of the temperature sensor means indicates the temperature of the region.

8. An electromagnetic hyperthermia system according to claim 7 wherein said inner conductor terminates in a means for increasing the capacitive coupling to the microwave energy towards the conductive tip thereby providing uniform heat distribution towards the conductive tip.

9. An electromagnetic hyperthermia system according to claim 8 wherein the means for increasing the capacitive coupling includes a plurality of stepped diameters for the conductive tip.

10. An electromagnetic hyperthermia system according to claim 7 wherein the conductive tip includes a conductive ring operatively connected to the end of the inner conductor and to a first end of the conductive tip, the conductive tip extending backwardly from the first end to a second end intermediate to the outer and inner conductor ends, the temperature sensor means including a temperature sensor operatively connected to the second end of the conductive tip for operative connection to the inner conductor, and a high resistive lead operatively connecting the temperature sensor to the outer conductor whereby the temperature sensor is positioned free to the electric field inside the outer conductor.

11. An electromagnetic hyperthermia system according to claim 1 wherein the outer conductor is broken to form a plurality of sections having first and second ends, a plurality of high resistive leads operatively interconnecting the plurality of sections of the outer conductor to the outer conductor, and wherein the temperature sensor means includes a plurality of temperature sensors operatively connected to the inner conductor, and a corresponding plurality of diodes, said plurality of diodes operatively connected to the outer conductor sections and to the temperature sensors whereby the diodes together with the direction of current flow produces a resistive measurement indicative of the temperatures of the sensor locations.

12. A method for operating a hyperthermia electromagnetic radiation applicator system including a plurality of applicators, a temperature sensing device for indicating temperature variations in surrounding body tissue, and a control means said method comprising:
 (a) providing direct current energy while simultaneously and intermittently providing microwave energy from the microwave energy sensors through the multiplexer to the plurality of applicators;
 (b) measuring the direct current voltage change across the applicators during the application of and during the absence of the microwave energy;
 (c) subtracting the measured dc voltage obtained during the absence of microwave energy from the voltage obtained in the absence of the high frequency energy to determine the temperature change for estimating surrounding tissue temperature;
 (d) comparing the signals indicative of the estimated temperature to signals idicative of a desired temperature pattern for determining microwave energy correcting signals; and
 (e) correcting the microwave energy input to the applicators for obtaining the desired heat pattern.

* * * * *